United States Patent [19]

Hughes

[11] Patent Number: 4,978,229

[45] Date of Patent: Dec. 18, 1990

[54] METHOD AND APPARATUS FOR TESTING THERMAL CONDUCTIVITY

[75] Inventor: John T. Hughes, Worcester, United Kingdom

[73] Assignee: Zortech International Limited, Droitwich, United Kingdom

[21] Appl. No.: 356,145

[22] Filed: May 25, 1989

[30] Foreign Application Priority Data

May 24, 1988 [GB] United Kingdom ............... 881258

[51] Int. Cl.$^5$ ........................................... G01N 25/18
[52] U.S. Cl. ........................................ 374/30; 374/10; 374/44
[58] Field of Search .................. 374/10, 29, 30, 43, 374/44, 112

[56] References Cited

U.S. PATENT DOCUMENTS

| 1,528,383 | 3/1925 | Schmidt | 374/30 |
| 2,323,715 | 7/1943 | Kuehni | 374/44 |
| 3,765,238 | 10/1973 | Sumikama et al. | 374/30 |
| 4,024,751 | 5/1977 | Potrzebowski | 374/43 |
| 4,534,663 | 8/1985 | Poppendiek et al. | |

OTHER PUBLICATIONS

Technology Applications: Pipe Insulation Tester, Oak Ridge National Laboratory No. 329X, Apr. 1979.
Abstract of Japanese Patent Specification No. 59-15 846, Heat Conductivity Measuring Cell Using Heat Generator, May 14, 1984, vol. 8, No. 105 (P-274) [1542].
Abstract of Japanese Patent Specification No. 56-148 045, Thermal Insulating Performance Testing Method, Feb. 23, 1982, vol. 6, No. 30 (P-103) [908].

*Primary Examiner*—Daniel M. Yasich
*Attorney, Agent, or Firm*—Browdy and Neimark

[57] ABSTRACT

Apparatus for testing material for thermally insulating pipes comprises a closed loop of pipe in a square configuration with an electric heater mounted coaxially within it. Thermocouples are attached to the pipe from the inside, and they and the heater are accessible via removable caps at the corners of the square. The pipe is suspended from a support framework by rods of low thermal conductivity welded to the inside corners of the square. The insulating material is applied to the pipe, and additional thermocouples fixed to its exterior. The heater is energized and the steady-state temperatures inside and outside the insulating material are measured. The configuration of the apparatus enables corrections for non-uniformity of heat loss and leakage through the rods to be readily made. Thus thermal conductivity values accurately representative of the performance of the insulating material in actual operation can be derived from the temperature measurements.

22 Claims, 4 Drawing Sheets

METHOD AND APPARATUS FOR TESTING THERMAL CONDUCTIVITY

This invention relates to methods and apparatus for testing the thermal conductivity of thermal insulating materials, in particular insulating material which is non-planar in form such as for insulating pipes.

BACKGROUND OF THE INVENTION

The thermal conductivity of thermal insulating material is a primary characteristic to be taken into consideration when designing and comparing insulation systems. Thus it is clearly wasteful to use more of an expensive insulating material than is actually necessary to obtain a required level of insulation, but it is also vital to ensure that sufficient insulating material is provided to achieve that level. The calculation of the appropriate quantity of insulating material involves knowledge of the thermal conduction characteristics of the insulation system. This parameter is dependent both on the inherent thermal conductivity properties of the material and on the environmental and geometric conditions in which it is to be used. Thus the actual temperatures and shapes of the thermal insulating components must be taken into account.

This can lead to difficulties in the design of efficient and cost-effective insulating systems for pipes, for example. The thermal conductivity of insulating material for use with pipes can in principle be measured on a standard flat plate tester. In such a device a heater plate which is typically square is surrounded at its periphery by a guard ring which prevents heat loss from the edge of the plate. Flat sheets or panels of the thermal insulation material to be tested are placed on both faces of the plate and extend to cover the guard ring. The plate, which defines the test section, is heated and the guard ring is also heated to match the plate temperature. The thermal conductivity of the insulation is calculated from measurements of the temperatures on its hot and cold faces and of the heat flowing through it. However, the conductivity value obtained is not necessarily representative of the behaviour of the insulating material when installed around a pipe. If the insulating material is fibrous, for example, the orientation of the fibres can affect the conductivity. Thus any difference in the fibre orientation as between the tester and the installed insulation may result in the measured conductivity being unrepresentative of the actual insulation system. Furthermore, the effective conductivity of the entire installed system is affected by factors such as heat transfer at butt joints in the insulation or at gaps which are created by thermal expansion, and the effect of any supporting and protective structure such as a metal casing. The effect of these factors is not included in the value obtained with a flat plate tester.

In view of these limitations, it is preferable to test pipe insulation in a configuration more closely resembling its actual conditions of use. In order to measure the thermal conductivity of insulating material applied to a pipe it is necessary to know the temperature difference across the insulation, the quantity of heat passing through a unit length of the insulation and the physical dimensions of the insulation. The conductivity L is given by $$= (Q \times ln(D/d))/(2 \times pi \times (t-T))$$

where
Q is the heat flow per unit length of the pipe;
D is the outer diameter of the insulation;
d is the inner diameter of the insulation;
pi = 3.1415O26;
t is the temperature at the inner surface of the insulating material; and
T is the temperature at the outer surface of the insulating material.

Two alternative procedures have been developed in the past for measuring conductivity values of pipe insulation. However, both have their own disadvantages. In a first method a straight section of insulated pipe is heated by means of electric heating elements wound around it, inside the insulating material. Thermocouples are attached to the pipe, in particular at two locations intermediate the mid-point of the pipe and each end. The central section of pipe, between these intermediate locations, is considered as being the actual test section and the end sections are treated as guard sections to compensate for end effects. Each section is provided with its own heating element or elements. The electric power supplied to the heating elements is adjusted for each section individually until a steady state is attained with no temperature gradient at the boundaries between the ends of the test section and the adjacent guard sections. It is assumed that in this state there are no losses of heat through the ends of the test section, so that all the heat supplied by that section's heating elements is traversing the insulating material around that section. Thus the heat loss per unit area of the pipe surface can be obtained and a value of thermal conductivity derived. However, this technique assumes that there is no heat transfer between the test section and the guard sections either through the pipe wall or along the interior of the pipe. In practice this requires very elaborate and cumbersome arrangements, and even then not all heat leakage may be eliminated, leading to inaccuracies in the result. Furthermore, establishing the required condition of no temperature gradient can be difficult and time-consuming.

A second method involves two straight pipes, one of which is longer than the other. The longer pipe is considered as having a central test section between guard sections each of which is half the length of the shorter pipe. Typically the pipes might be three meters and one meter long, giving a test section of two meters between half-meter guard sections. The thermal behaviour of the two halves of the shorter pipe is assumed to be identical to that of the guard sections in the longer pipe. Each pipe is fitted with heating elements, thermocouples and insulation in a similar manner to the first technique. Both pipes are heated to a range of temperatures and the electric heating energy supplied to obtain a steady state is plotted against the average pipe temperature. The difference in heat energy supplied to the two pipes is attributed to the heat loss from the centre test section of the longer pipe. In practice it is very difficult or impossible to create conditions in the short pipe that are identical to those in the guard sections in the longer pipe, and the results are correspondingly inaccurate.

It is an object of this invention to provide a method of testing the thermal conductivity of non-planar insulating material such as pipe insulation, which avoids or alleviates the problems and inaccuracies encountered with known test methods. It is also an object of the invention to provide an apparatus for performing the method.

SUMMARY OF THE INVENTION

According to one aspect of this invention there is provided a method of testing the thermal conductivity of non-planar thermal insulating material, in which a length of pipe arranged as a closed loop is surrounded with thermal insulating material extending along the pipe. A temperature gradient is established between an interior region of the pipe and an exterior region of the insulating material, for example by means of an electric heater located inside the pipe. The temperature difference thus established between inner and outer sides of the insulating material is measured, and an indication of the thermal conductivity of the insulating material is derived from this temperature difference.

With this method there are no isolated pipe ends, and therefore no associated heat losses which perturb the measurement and which are difficult to quantify. The main causes of heat loss or other perturbation are the pipe supports and any corners that may be present. These losses can be minimised and/or measured or otherwise assessed accurately.

According to another aspect of this invention there is provided an apparatus for testing the thermal conductivity of non-planar thermal insulating material, including a length of pipe arranged as a closed loop and shaped for thermal insulating material to surround the pipe and extend along it. Means such as an electric heater is disposed within the pipe for establishing a temperature gradient between an interior region of the pipe and an exterior region of the insulating material. Temperature sensing means, for example thermocouples, is provided for measuring temperature difference between inner and outer sides of the insulating material, whereby an indication of thermal conductivity of the insulating material may be derived from the temperature difference.

The loop may be in any of several shapes, such as a ring or a hexagon, but one convenient shape is a square. Preferably the pipe has at least one portion forming a removable cover providing access to the interior of the pipe, and in the case of a square loop this cover portion may be located at a corner of the square.

The means for establishing a temperature gradient typically comprises an electric heater disposed within the pipe. However, the apparatus may equally be used for testing insulating material for keeping pipes cold, in which case a cooling device could be used in place of a heater. The heater (or cooling device) may be mounted generally coaxially within the pipe, for example suspended on spider members engaging the inside surface of the pipe.

Preferably the pipe is suspended on rods of low thermal conductivity material within a supporting framework. These rods may be of low thermal conductivity steel, and, if the loop is square, may be secured (for example by welding) to the inside corners of the square.

The temperature sensing means may include thermocouples, located for example in holes drilled in the pipe or in grooves formed in its outer surface. Typically thermocouples arc provided to measure the temperatures of the inner and outer sides of the insulating material individually, and the temperature difference is derived from the individual measurements.

BRIEF DESCRIPTION OF THE DRAWINGS

A method and apparatus for testing pipe insulating materials in accordance with this invention will now be described, by way of example, with reference to the accompanying drawings, in which.

DESCRIPTION OF THE PREFERRED EMBODIMENTS

Figure 1:
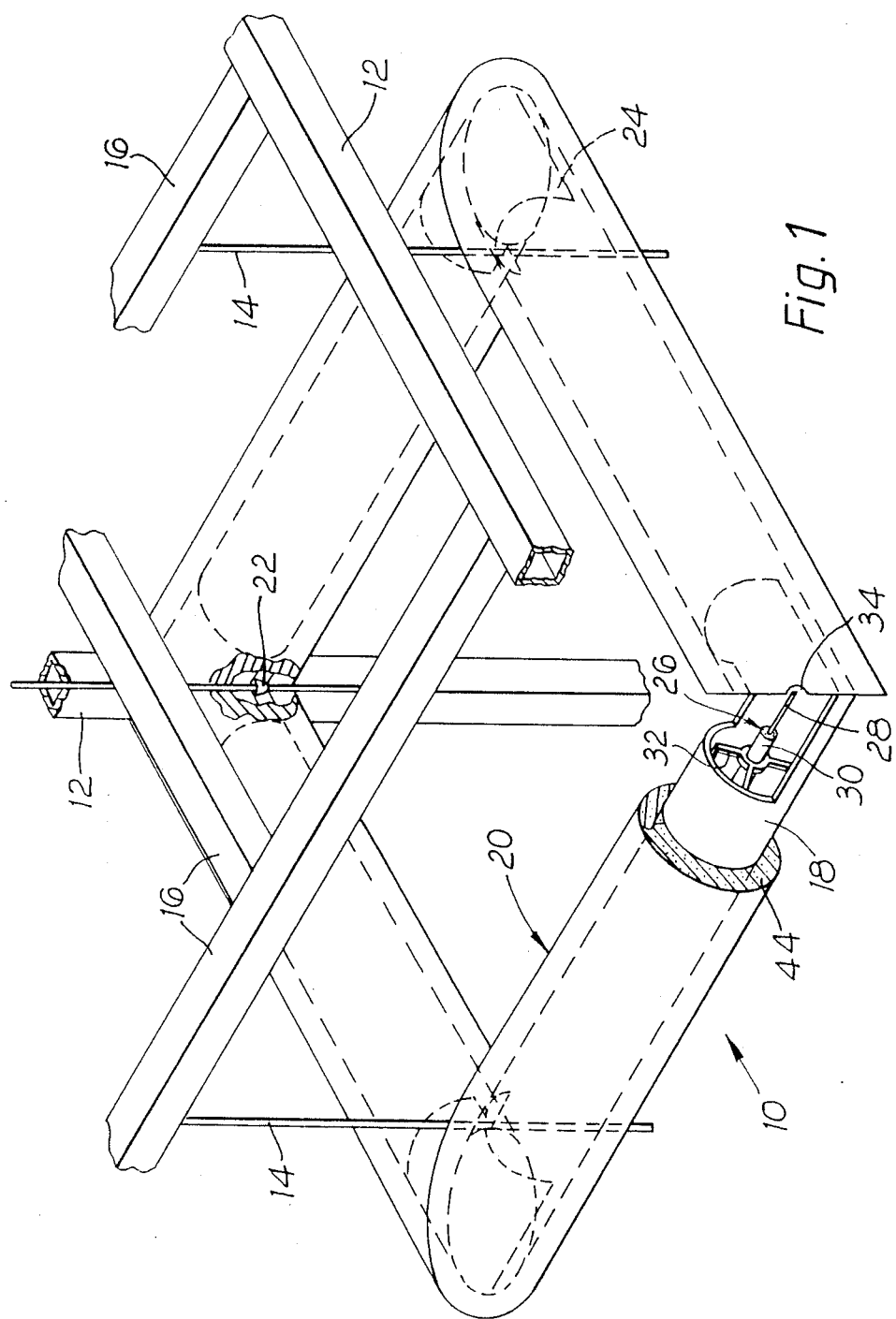
FIG. 1 is a partly cut-away isometric view of the apparatus, fitted with insulation to be tested.
Figure 2:
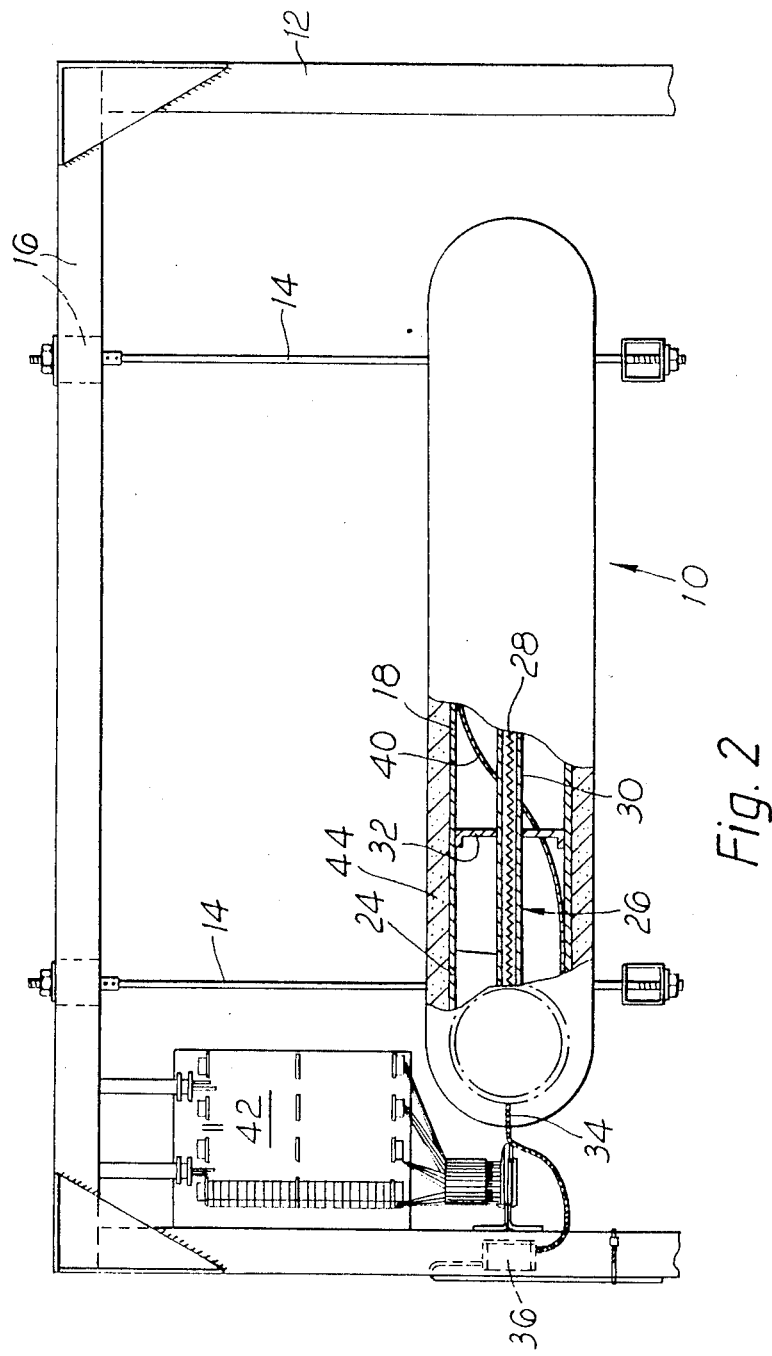
FIG. 2 is a partly sectioned side elevation of the apparatus.

Referring to FIG. 1, a pipe insulation tester 10 is housed in a generally box-like framework 12 (shown partly cut-away) and suspended by rods 14 from an H-frame 16 (also shown partly cut-away) spanning the top of the framework. The tester 10 essentially comprises four lengths of pipe 18 which are mitred and welded at their ends to form a closed square loop 20. This pipe is made of a high temperature stainless steel or nickel-chromium alloy, able to withstand operation at up to 1000 degrees C. In the illustrated embodiment the pipe is circular in cross-section, but this and the pipe cross-sectional dimension will depend on the intended use of the insulating material to be tested. Actual pipe outer diameters for which the apparatus has been constructed are of the order of 80 and 140 mm, with wall thicknesses of 4 mm and 8 mm respectively. The size of the square loop 20 is preferably as large as possible (for example at least six times the cross-sectional dimension of the pipe 18), in order to minimise the contribution of the corners to the heat dissipation of the tester 10, but we have found that a square loop one meter on a side provides satisfactory results.

The rods 14, which are of a low thermal conductivity material such as a nickel-chromium alloy, are welded to the inside corners of the loop as at 22, and secured by nuts at their upper ends to the H-frame 16. The welds 22 extend only up to the mid-line of the pipe 18, leaving free a separate cap section 24 at each corner which can be removed to provide access to the interior of the pipe 18.

Within the pipe 18 there is a 3 kW electric heater 26 comprising a helical coil 28 of bare resistance wire, such as nickel-iron-chromium or iron-aluminium, within a tube 30 of fused silica. This tube is supported generally coaxially within the pipe 18 by stainless steel spiders S2 extending between the tube 30 and the inside wall of the pipe 18. Power leads from the heater 26 extend out of the pipe 18 via a small access hole 34 at one corner to a terminal block 36 mounted on the framework 12.

Figure 3:
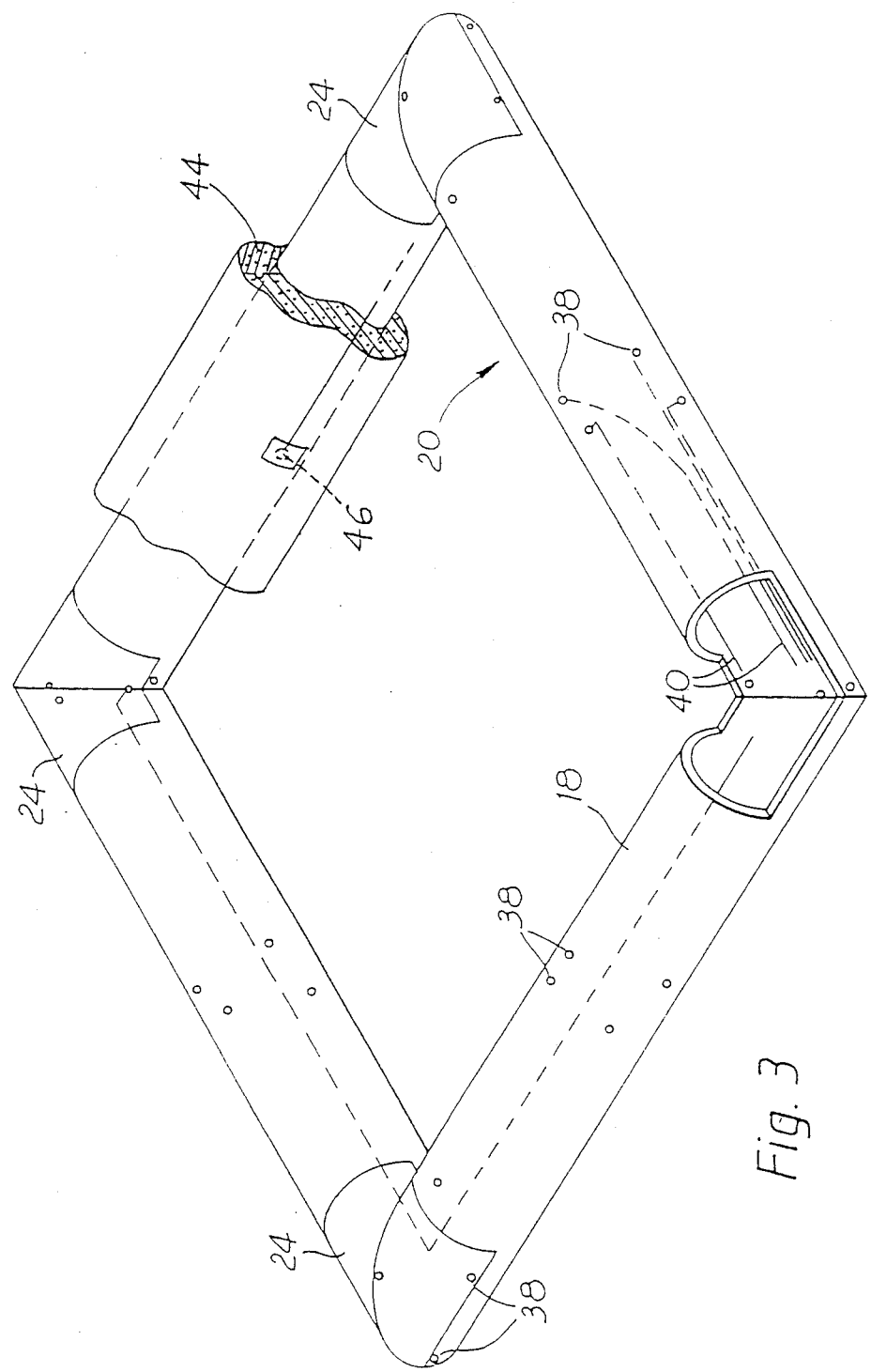
FIG. 3 is a partly cut-away isometric view showing the location of thermocouples forming part of the apparatus.

As shown in FIG. 3, thirty-two thermocouples 38 are mounted in eight groups of four in the pipe 18, with a respective group being located at each corner and at the mid-point of each side of the loop 20. The four thermocouples S8 within each group are spaced a quarter of the pipe circumference from one another, offset by about 10 degrees from the vertical and horizontal planes through the pipe axis. This offset is provided so that the thermocouple positions do not coincide with, for example, horizontal or vertical joints between part-cylindrical sections of insulation. The thermocouples 38 are K-type devices sheathed in stainless steel and 1 mm in diameter. Depending on the pipe size, leads 40 from the thermocouples 38 may be housed within the pipe 18 and extend along it from the access hole S4 to holes drilled through the pipe wall at the locations shown in FIG. 3. These holes receive the temperature sensitive thermocouple junctions which lie therein flush with the outer surface of the pipe 18. Thus these thermocouples S8 can measure the temperature at the inner side of insulating material placed around the pipe as hereinafter described. If the bore of the pipe 18 is too narrow to accommodate the thermocouple leads 40, they may instead be disposed in grooves machined along the outer surface of the pipe 18. The thermocouple leads 40 extend through the access hole 34 to a junction box 42, from which connection can be made to appropriate measuring devices such as electronic voltmeters.

Insulating material 44 to be tested is applied to the pipe 18 in any conventional manner appropriate to the nature of the material. Thus a fibrous material would typically be wrapped around the pipe 18 and secured using a sheet metal covering. Semi-cylindrical sections moulded from a microporous insulating material, as described in European patent specification No. 0 212 872/U.S. Pat. No. 4 801 415, can be fitted to enclose the pipe 18 and then secured with flexible metal bands.

Additional thermocouples (one of which is shown at 4b in FIG. 3) are then taped to the exterior of the insulating material 44 to measure the temperature at its outer side. Any desired surface treatment may then be applied to the insulating material 44 to reproduce the anticipated operating configuration of the material 44 when in use.

The insulating characteristics of the material 44 are tested by energising the heater 26 for a period sufficient for the temperatures indicated by the thermocouples at its inner and outer sides to attain a steady state. The temperatures and heater power arc then recorded and used to calculate the thermal conductivity in accordance with the equation given above.

Correction may be made for the non-uniformity of heat loss at the corners of the test arrangement, by varying the pitch of the helical coil 28 in the heater 26. However, we have found in practice that even with a uniform coil 28 there is little difference in pipe temperatures on straight sections as compared to corners. Thus we believe that errors arising from the omission of such correction would be no more than 1 or 2%.

Allowance is made for the heat losses through the support rods 14 by measuring the temperature gradient along the rods 14 and calculating the heat flow corresponding to the measured gradient.

We have found that the closed-loop tester 10 described above provides a simple, expedient and accurate way of testing insulating materials for use on pipes. The values of thermal conductivity obtained agree closely with those predicted by calculation from theory. Even with a square loop 20 as shown in the figures, the temperature distribution over the insulating material 44, especially on its inner surface, is remarkably uniform. This is desirable, since the equation given above requires the use of average values T and t for the temperatures inside and outside the insulating material 44. We have found that there is some variation in temperature on the outer surface of the insulating material 44, because heat loss is a function of both temperature and surface orientation, so the variation in orientation of the surface around the circumference of the pipe 18 produces a corresponding variation in temperature. However, for outside surface temperatures in the range 20 to 100 degrees C and a temperature difference across the insulating material 44 of the order of 500 degrees C, we have observed a temperature variation of +/- 10 degrees C. Thus the use of an averaged temperature introduces only a small error, of the order of 1% or less.

The use of a closed loop 20 has the advantage that the whole of the pipe 18 and the insulating material 44 are included in the test measurements, so there is no necessity for estimates of end losses nor for special steps such as balancing of temperatures between test and guard sections. All of the heat supplied to the pipe loop 20 must pass through the insulating material 44, so the heat transfer through the material 44 can be derived accurately and directly from the power input to the heater 26. A single power control and wattmeter are sufficient, and the measurements for determining the conductivity for any given heat level can be completed in a relatively short time (typically ten hours).

Insulation systems incorporating components additional to the actual insulating material 44, such as metal cladding or radiation shields, can be tested to determine the overall performance of the complete system of insulating material 44 together with the other components. This permits the effect of heat bridges, such as metal cladding, to be assessed accurately. Similarly, the practical results of differences in thermal expansion as between the pipe 18 and the insulating material 44 (leading to gaps at joints) are readily taken into account. However, if absolute values of thermal conductivity of the insulating material 44 are required, it is possible for example to fit the material 44 to the pipe 18 in a hot condition to avoid the presence of expansion gaps.

The simplicity of the test arrangement means that it is relatively inexpensive to manufacture, is compact and easily moved, and requires little skill or experience for its operation. Furthermore, the simple nature of its principle of operation, and in particular the fact that all heat supplied must pass through the insulating material under test, makes analysis of the measurements to derive an accurate conductivity value a straightforward procedure.

Figure 4:
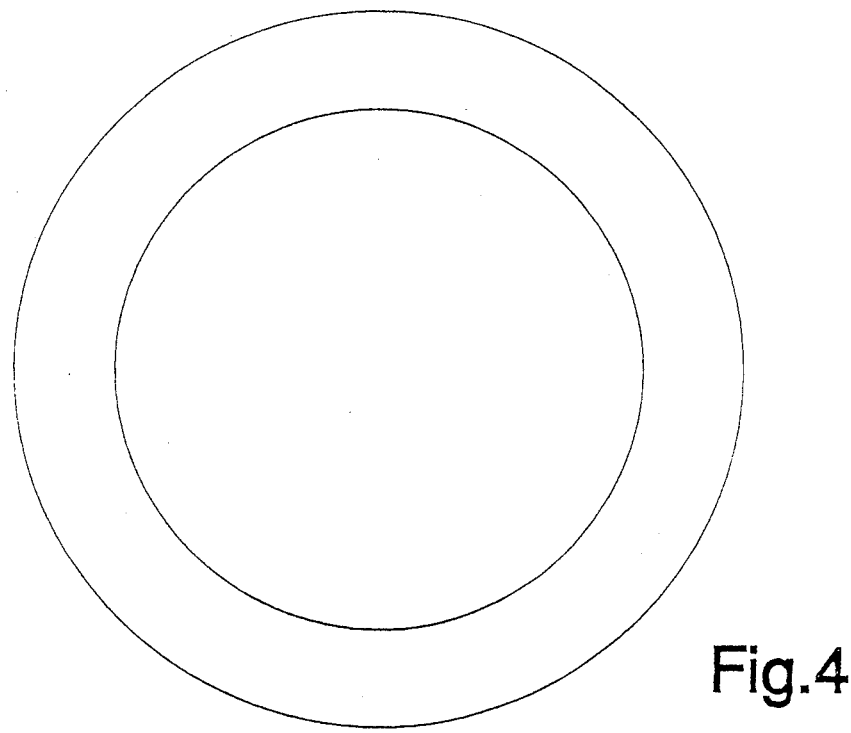
FIGS. 4 and 5 show alternative shapes for the apparatus.
Figure 5:
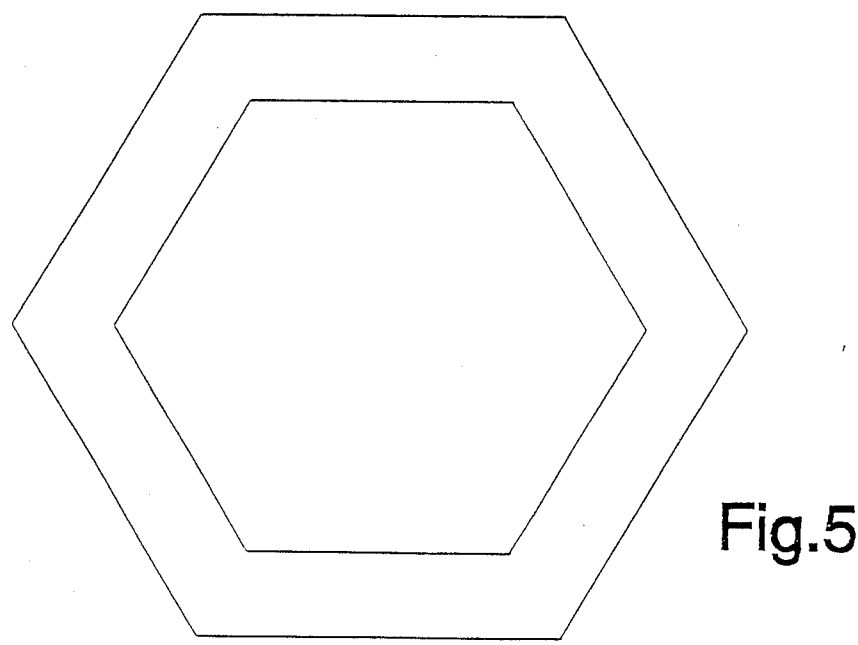

As noted above, the loop may have a shape other than a square, for example a ring or a hexagon as shown in outline in FIGS. 4 and 5 respectively.

I claim:

1. A method of testing the thermal conductivity of non-planar thermal insulating material, comprising:
   surrounding a length of pipe with thermal insulating material extending along the pipe, said pipe being arranged as a closed loop, whereby a simulation is provided of actual conditions of use of insulation on insulated pipes;
   establishing a temperature gradient between an interior region of said pipe and an exterior region of said insulating material;
   measuring a temperature difference between inner and outer sides of said insulating material; and
   deriving an indication of thermal conductivity of said insulating material from said temperature difference.

2. The method of claim 1, wherein said temperature difference is a steady state temperature difference.

3. The method of claim 1, including the step of disposing temperature sensing means inside and outside said insulating material.

4. The method of claim 1, wherein supports are provided for said pipe, including the step of applying a correction to said indication of thermal conductivity to compensate for heat losses via said supports.

5. Apparatus for testing the thermal conductivity of non-planar thermal insulating material, comprising:
   a length of pipe arranged as a closed loop and shaped for thermal insulating material to surround said pipe and extend therealong, whereby a simulation is provided of actual conditions of use of insulation on insulated pipes;
   means disposed within said pipe for establishing a temperature gradient between an interior region of said pipe and an exterior region of said insulating material; and
   temperature sensing means for measuring temperature difference between inner and outer sides of said insulating material, whereby an indication of thermal conductivity of said insulating material is derived from said temperature difference.

6. The apparatus of claim 5, wherein said loop is in the shape of a square.

7. The apparatus of claim 6, wherein the ratio of length of one side of said square to cross-sectional dimension of said pipe is at least six.

8. The apparatus of claim 5, wherein the pipe has at least one portion forming a removable cover providing access inside the pipe.

9. The apparatus of claim 8, wherein said loop is in the shape of a square and said removable cover portion is located at a corner of said square.

10. The apparatus of claim 5, wherein said loop is in the shape of a ring.

11. The apparatus of claim 5, wherein said loop is in the shape of a hexagon.

12. The apparatus of claim 5, wherein said means for establishing a temperature gradient comprises an electric heater disposed within said pipe.

13. The apparatus of claim 12, wherein said heater is mounted generally coaxially within said pipe.

14. The apparatus of claim 12, wherein said heater is suspended on spider members engaging an inside surface of said pipe.

15. The apparatus of claim 12, wherein said heater comprises a wire heating element within a silica tube.

16. The apparatus of claim 12, wherein said heater is arranged to provide non-uniform heating.

17. The apparatus of claim 5, wherein said pipe is suspended on rods of low thermal conductivity material.

18. The apparatus of claim 17, wherein said rods are of low thermal conductivity metal alloy.

19. The apparatus of claim 17, wherein said loop is in the shape of a square and said rods are secured to inside corners of said square.

20. The apparatus of claim 5, wherein said temperature sensing means comprises thermocouples.

21. The apparatus of claim 20, wherein at least one of said thermocouples is located in a hole drilled in said pipe.

22. The apparatus of claim 20, wherein at least one of said thermocouples is located in a groove formed in an outer surface of said pipe.

* * * * *